United States Patent
Vlahos

(10) Patent No.: US 7,118,589 B2
(45) Date of Patent: Oct. 10, 2006

(54) LIGHT THERAPY EQUIPMENT

(76) Inventor: George J. Vlahos, 8549 Heather Ct., St. John, Lake County, IN (US) 46373

( * ) Notice: Subject to any disclaimer, the term of this patent is extended or adjusted under 35 U.S.C. 154(b) by 624 days.

(21) Appl. No.: 10/633,741

(22) Filed: Aug. 4, 2003

(65) Prior Publication Data

US 2005/0021111 A1    Jan. 27, 2005

Related U.S. Application Data

(62) Division of application No. 10/064,010, filed on Jun. 4, 2002.

(60) Provisional application No. 60/295,747, filed on Jun. 4, 2001.

(51) Int. Cl.
*A61N 5/06*   (2006.01)

(52) U.S. Cl. ............................................ 607/94; 607/88

(58) Field of Classification Search ................ 607/88, 607/94; 250/492.1; 606/9
See application file for complete search history.

(56) References Cited

U.S. PATENT DOCUMENTS

| | | | | |
|---|---|---|---|---|
| 2,003,527 A | * | 6/1935 | Bacon et al. ................. | 607/94 |
| 2,506,308 A | * | 5/1950 | Maynier ....................... | 602/30 |
| 2,568,934 A | * | 9/1951 | Schenker ..................... | 607/148 |
| 3,366,105 A | * | 1/1968 | Sadowski et al. ............. | 601/16 |
| 4,612,444 A | * | 9/1986 | Ragusa ....................... | 250/492.1 |
| 4,731,541 A | * | 3/1988 | Shoemaker ............. | 250/504 R |
| 4,979,523 A | * | 12/1990 | Grimm ........................ | 132/73.5 |
| 4,988,883 A | * | 1/1991 | Oppawsky ................. | 250/492.1 |
| 5,130,551 A | * | 7/1992 | Nafziger et al. ........... | 250/492.1 |
| 5,130,553 A | * | 7/1992 | Amoh ....................... | 250/492.1 |
| 5,466,248 A | * | 11/1995 | Whitson-Newman ........ | 607/88 |
| 6,254,625 B1 | * | 7/2001 | Rosenthal et al. ............. | 607/88 |
| 6,960,201 B1 | * | 11/2005 | Cumbie ........................... | 606/9 |
| 2003/0153962 A1 | * | 8/2003 | Cumbie ........................ | 607/94 |
| 2004/0098071 A1 | * | 5/2004 | Chapman et al. ............. | 607/94 |

* cited by examiner

*Primary Examiner*—Henry M. Johnson, III

(57) ABSTRACT

Apparatuses adopted to provide light therapy to regions of the body that cannot be conveniently exposed to the sun or conventional tanning equipment. Four embodiments of the invention include a tanning bed 10 with an adjustable leg support 12 that allows tanning of the buttocks and rectal and genital areas of a person lying on the bed 10, a toilet (water closet) 20 equipped with one or more tanning lamps 26 for tanning the rectal and genital areas of a person sitting on the toilet 20, a foot and hand tanning apparatus 40 comprising a flexible block 42 with slots 44 for receiving the toes or fingers 48 of a person, and a tanning recliner 50 with tanning lamps 56 located within for tanning the skin of the user reclining on the recliner 50.

1 Claim, 2 Drawing Sheets

LIGHT THERAPY EQUIPMENT

CROSS REFERENCE TO RELATED APPLICATIONS

This application claims the benefit of U.S. Provisional Application No. 60/295,747, filed Jun. 4, 2001. This is a division of application Ser. No. 10/064,010 filed Jun. 4, 2002.

BACKGROUND OF INVENTION

1. Field of the Invention

The present invention generally relates to equipment for providing light therapy to regions of the body that cannot be conveniently exposed to the sun or conventional tanning equipment.

2. Description of the Prior Art

Various tanning equipment are known, such as those disclosed in U.S. Pat. Nos. 2,054,332, 4,130,120, 4,424,598, 4,945,908, 4,989,600, 5,086,769, 5,117,842 and 5,466,248. Each of these patents discloses some type of tanning equipment for providing light therapy. For example, U.S. Pat. No. 4,130,120 discloses a bathing chamber with sun lamps controlled by a timer, and U.S. Pat. No. 5,086,769 discloses a tanning chair that can be converted Into a couch. The chair is oriented as a recliner and can be equipped with a variety of conveniences. Finally, U.S. Pat. Nos. 2,054,332, 5,117, 842 and 5,466,248 are all related to the treatment of feet with light therapy, with U.S. Pat. No. 5,117,842 being directed to a device capable of providing for tanning between the toes.

SUMMARY OF INVENTION

The present invention provides four embodiments of apparatuses adopted to provide light therapy to regions of the body that cannot be conveniently exposed to the sun or conventional tanning equipment. The four embodiments include a tanning bed with an adjustable leg support that allows tanning of the buttocks and rectal and genital areas of a person lying on the bed, a toilet (water closet) or toilet seat equipped with one or more tanning lamps for tanning the rectal and genital areas of a person sitting on the toilet seat, a foot and hand tanning apparatus comprising a flexible block with slots for receiving the toes or fingers of a person, and a tanning recliner with tanning lamps located within for tanning the skin of the user reclining on the recliner.

Other objects and advantages of this invention will be better appreciated from the following detailed description.

DETAILED DESCRIPTION

The present invention provides four apparatuses for providing light therapy to regions of the body that cannot be conveniently exposed to the sun or conventional tanning equipment. Each of these apparatuses may be equipped with a controller and timer to regulate the exposure time.

Figure 1:
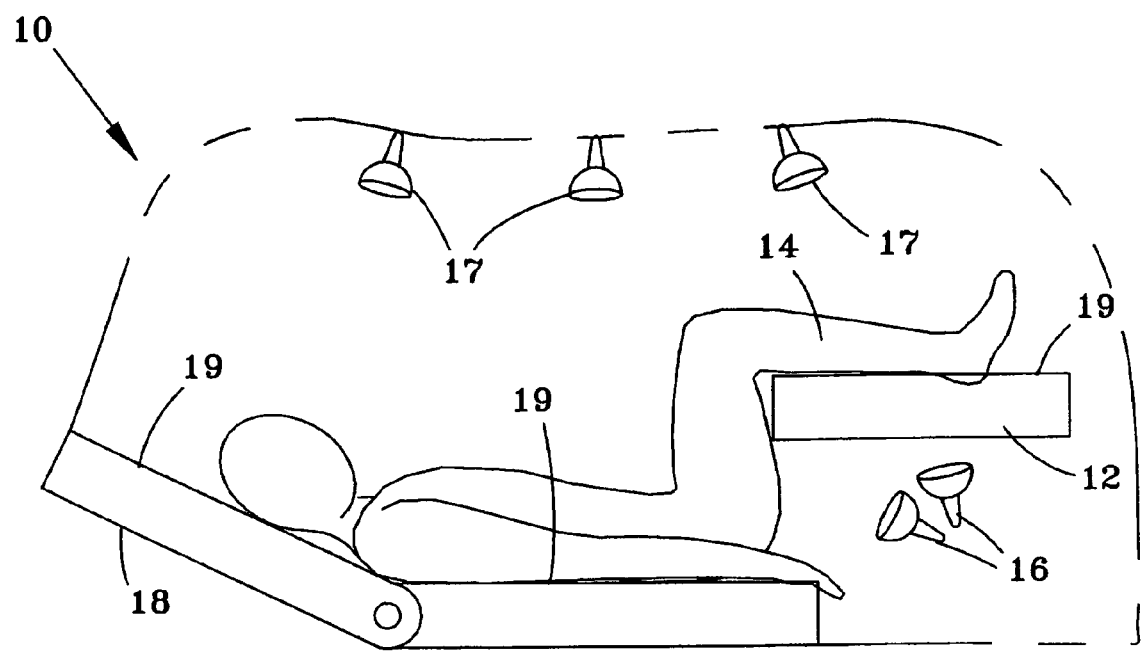
FIG. 1 is cross-sectional view of a tanning bed in accordance with a first embodiment of this invention.

FIG. 1 represents a tanning bed 10 with an adjustable leg support 12 adapted to raise the legs 14 of the user to expose the buttocks (including the rectal and genital areas) and the backs of the thighs to one or more conventional ultraviolet (UV) or tanning lamps 16 mounted so as to be located beneath the leg support 12 when raised. The tanning lamps 16 provide for tanning of the buttocks and rectal and genital areas of a person lying on the bed 10. Additional tanning lamps 17 can be placed above the bed 10 for tanning the upper surface areas of the person. Preferably, as represented in FIG. 1, the thighs are raised to be oriented substantially vertical, while the lower legs are substantially horizontal for comfort. The leg support 12 can be lowered for use as a conventional flat tanning bed 10. The portion 18 of the bed supporting the upper torso and head of the user can preferably be tilted or raised for comfort. The upper surface 19 of the tanning bed 10 on which the user reclines may be an air mattress for comfort.

Figure 2:
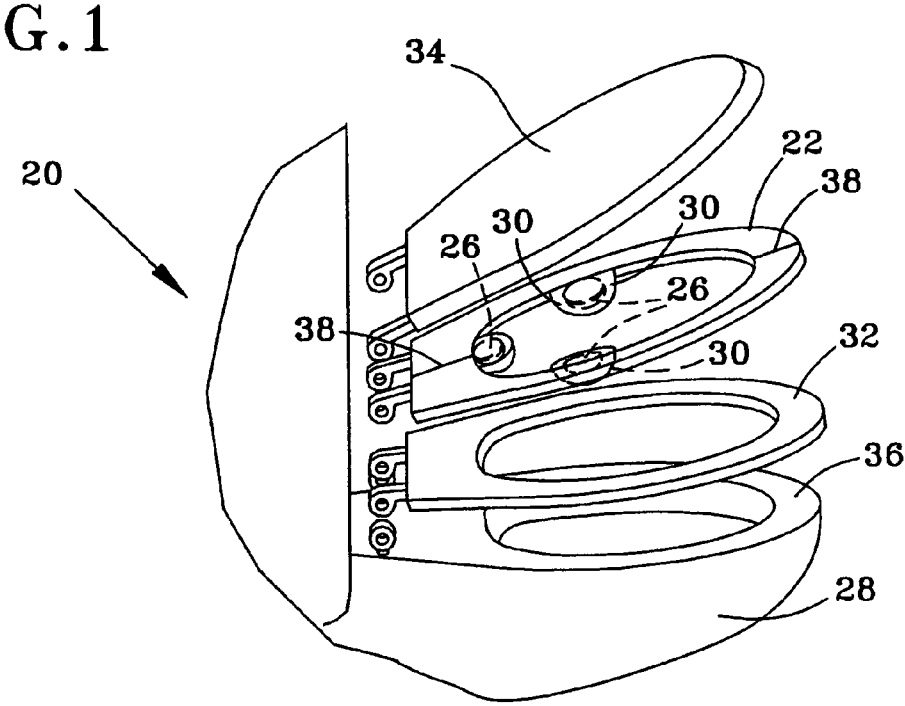
FIGS. 2 and 3 are side and plan views of a toilet equipped with a toilet seat for providing light therapy in accordance with a second embodiment of this invention.
Figure 3:
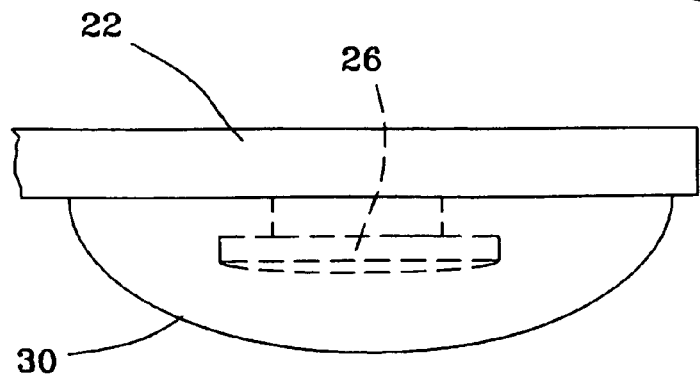

FIGS. 2 and 3 represent a toilet (water closet) 20 having a toilet seat 22 equipped with one or more tanning lamps 26 to provide light therapy to the rectal and genital areas of a person sitting on the seat 22. As shown, a lamp 26 is positioned at each side of the seat 22, and projects downward into the toilet bowl 28. Alternatively or in addition, a lamp may be placed toward the rear of the seat 22. The lamps 26 are preferably encased in a waterproof UV-transparent cover 30 for protection and safety. The seat 22 to which the tanning lamps 26 are mounted is shown as a separate seat 22 that is hinged to the mounting hardware for an existing toilet seat 32, so as to be located between the existing toilet seat 32 and the existing seat cover 34. Alternatively, the lamps 26 may be permanently or removably mounted directly to the lower surface of the existing seat 32, or removably mounted from the rim 36 of the toilet bowl 28. Another alternative is to configure the seat 22 to be removably placed directly on the existing toilet seat 32. The seat 22 can then be readily removed and transported and even used with a chair. To facilitate transporting, the seat 22 may have a two-piece construction held together with hinges 38 that allow the seat 22 to be folded. In addition, this invention may be used with a bidet instead of a toilet.

Figure 4:
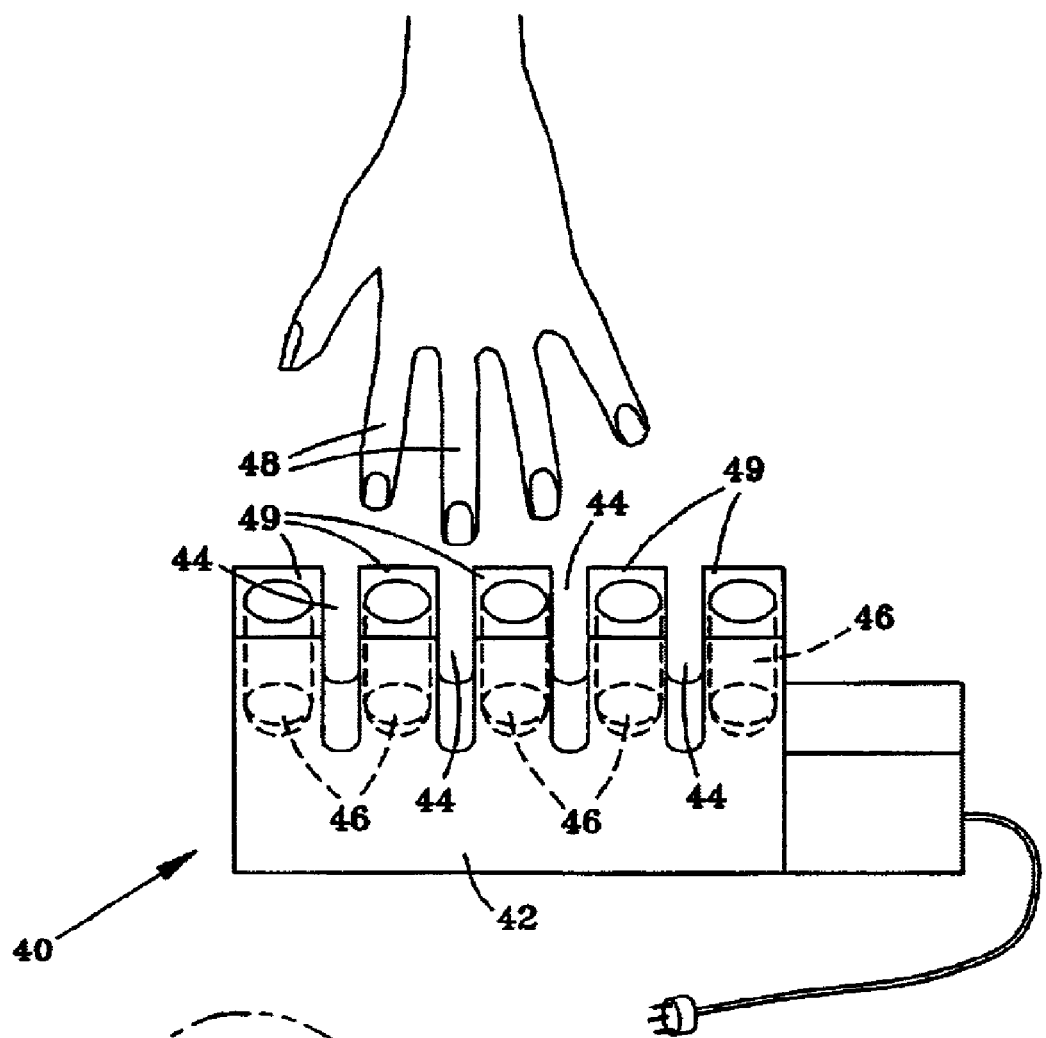
FIG. 4 shows an apparatus for providing light therapy between a person's toes and fingers in accordance with a third embodiment of this invention.

FIG. 4 represents a foot and hand tanning apparatus 40 comprising a flexible block 42 with slots 44 for receiving the toes or fingers (digits) 48 of a person. Tanning lamps 46 are provided in the portions 49 of the block 42 between the slots 44 for tanning the area of the skin between the toes/fingers 48. At least the surfaces of the slots 44 facing the toes/fingers 48 are transparent to the UV rays radiated by the lamps 46. The apparatus 40 may further include a lamp for tanning the bottom of the user's feet or the palm of the user's hands.

Figure 5:
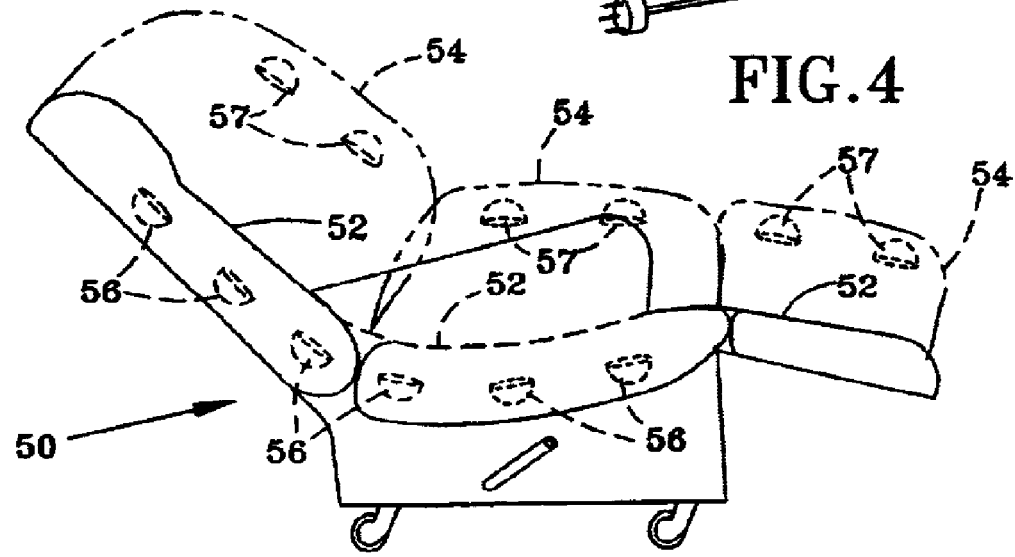
FIG. 5 is cross-sectional view of a recliner equipped for providing light therapy in accordance with a fourth embodiment of this invention.

FIG. 5 represents a tanning recliner 50 with an upper cover 54. Contrary to prior art tanning recliners in which tanning lamps are positioned above and to the sides of the user, the tanning recliner 50 is equipped with tanning lamps 56 located within the recliner 50, whose upper surface 52 is transparent to the desired UV rays radiated by the lamps 56 so as to provide tanning of those lower body surfaces facing and contacting the recliner surface 56. Additional tanning lamps 57 can be placed above the recliner 50 for tanning the upper surface areas of a person in the recliner 50. The recliner 50 can be sized to accommodate more than one person. The surface 56 of the recliner 50 on which the user reclines may be an air mattress for comfort.

While the invention has been described in terms of specific embodiments, it is apparent that other forms could be adopted by one skilled in the art. For example, various ultraviolet ray-generating devices could be used in place of the conventional UV lamps noted above. Therefore, the scope of the invention is to be limited only by the following claims.

What is claimed is:

1. A tanning apparatus comprising a flexible block (42) with a plurality of slots (44) sized for receiving individual digits (48) of a user, and ultraviolet ray-generating means (46) located in portions (49) of the block (42) between the slots (44) for tanning skin of the user between the digits (48) of the user when the digits (48) are received in the slots (44) wherein at least the surfaces of the slots (44) facing the digits are transparent to ultraviolet rays.

* * * * *